(12) United States Patent
Endou

(10) Patent No.: US 12,290,894 B2
(45) Date of Patent: May 6, 2025

(54) MONITORING DEVICE AND MONITORING METHOD

(71) Applicant: FANUC CORPORATION, Yamanashi (JP)

(72) Inventor: Takahiro Endou, Yamanashi-ken (JP)

(73) Assignee: FANUC CORPORATION, Yamanashi (JP)

( * ) Notice: Subject to any disclaimer, the term of this patent is extended or adjusted under 35 U.S.C. 154(b) by 325 days.

(21) Appl. No.: 18/021,828

(22) PCT Filed: Aug. 16, 2021

(86) PCT No.: PCT/JP2021/029853
§ 371 (c)(1),
(2) Date: Feb. 17, 2023

(87) PCT Pub. No.: WO2022/039116
PCT Pub. Date: Feb. 24, 2022

(65) Prior Publication Data
US 2023/0311264 A1 Oct. 5, 2023

(30) Foreign Application Priority Data
Aug. 21, 2020 (JP) .................. 2020-140280

(51) Int. Cl.
*B23Q 11/10* (2006.01)
*B23Q 11/12* (2006.01)
*B23Q 17/00* (2006.01)

(52) U.S. Cl.
CPC ............ *B23Q 17/007* (2013.01); *B23Q 11/10* (2013.01); *B23Q 11/126* (2013.01)

(58) Field of Classification Search
CPC ...... B23Q 11/10; B23Q 17/007; B23Q 11/126
See application file for complete search history.

(56) References Cited

U.S. PATENT DOCUMENTS

2017/0139432 A1* 5/2017 Endou ............... B23Q 11/10

FOREIGN PATENT DOCUMENTS

| JP | S5627570 U | 3/1981 |
| JP | S59162443 A | 9/1984 |

(Continued)

OTHER PUBLICATIONS

International Search Report issued by the Japanese Patent Office acting as the International Searching Authority in relation to International Application No. PCT/JP2021/029853 dated Oct. 19, 2021 (3 pages) along with English language translation (2 pages).

(Continued)

*Primary Examiner* — Jamel E Williams
(74) *Attorney, Agent, or Firm* — Robert P. Michal, Esq.; Carter, DeLuca & Farrell LLP

(57) ABSTRACT

Provided is a monitoring device and a monitoring method that can capture the condition of a coolant in detail. A monitoring device according to one embodiment includes: a first detection unit that detects a first physical quantity; a second detection unit that detects a second physical quantity; a ratio calculation unit that calculates the ratio between a first value obtained when the first physical quantity is expressed using a specified unit, and a second value obtained when the second physical quantity is expressed using a specified unit; and an inferring unit that, if the calculated ratio is above an upper limit value of a management range or below a lower limit value of the management range, infers that one among an oil and an electrolyte contained in the coolant is abnormal.

10 Claims, 2 Drawing Sheets

(56) References Cited

FOREIGN PATENT DOCUMENTS

| JP | S59210353 | A |   | 11/1984 | | |
|----|-----------|---|---|---------|---|---|
| JP | S60013252 | A |   | 1/1985 | | |
| JP | S63191514 | A |   | 8/1988 | | |
| JP | H04141319 | A |   | 5/1992 | | |
| JP | H0542414 | A |   | 2/1993 | | |
| JP | H09085577 | A |   | 3/1997 | | |
| JP | H1073583 | A |   | 3/1998 | | |
| JP | 2004156065 | A | * | 6/2004 | | |
| JP | 2006130603 | A | * | 5/2006 | | |
| JP | 2010188480 | A |   | 9/2010 | | |
| JP | 2011080814 | A |   | 4/2011 | | |
| JP | 2017087403 | A | * | 5/2017 | ............ | B23Q 11/10 |
| WO | 2006126248 | A1 |   | 11/2006 | | |

OTHER PUBLICATIONS

Written Opinion of the International Searching Authority issued by the Japanese Patent Office acting as the International Searching Authority in relation to International Application No. PCT/JP2021/029853 dated Oct. 19, 2021 (3 pages).

\* cited by examiner

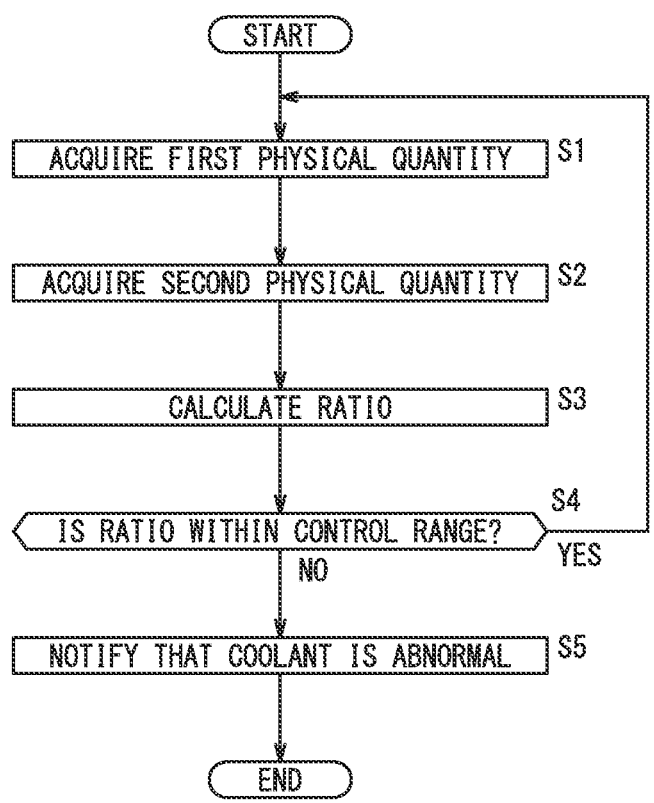

MONITORING DEVICE AND MONITORING METHOD

CROSS-REFERENCE TO RELATED APPLICATIONS

This application is a national phase entry under 35 U.S.C. 371 of PCT International Application No. PCT/JP2021/029853, filed Aug. 16, 2021, which claims priority to Japanese Patent Application No. 2020-140280, filed Aug. 21, 2020, the disclosure of each of these applications is expressly incorporated herein by reference in their entirety.

TECHNICAL FIELD

The present invention relates to a monitoring device and a monitoring method for monitoring a coolant used in a machine tool.

BACKGROUND ART

When machining a workpiece using a tool, a machine tool injects a coolant to a machined portion. The quality of the machined product may change depending on the change in the condition of the coolant.

JP 2017-087403 A discloses a control device for a machine tool. This control device calculates the rate of change in the hydrogen ion concentration or the like of a coolant. Further, when determining that the condition of the coolant has deteriorated according to the calculated rate, the control device causes the machine tool to execute an operation for improving the condition of the coolant.

SUMMARY OF THE INVENTION

However, the control device disclosed in JP 2017-087403 A simply monitors the rate of change in the hydrogen ion concentration or the like of the coolant. Therefore, it is not possible to determine which component of the coolant is in an abnormal condition (deteriorated condition). Therefore, there may be a case where the condition of the coolant is not improved even though the condition of the coolant is controlled to be improved.

Therefore, an object of the present invention is to provide a monitoring device and a monitoring method capable of grasping the condition of a coolant in detail.

According to a first aspect of the present invention, there is provided a monitoring device that monitors a coolant used in a machine tool, the monitoring device comprising: a first detection unit configured to detect a first physical quantity; a second detection unit configured to detect a second physical quantity different from the first physical quantity; a ratio calculation unit configured to calculate a ratio between a first value representing the first physical quantity in a predetermined unit, and a second value representing the second physical quantity in the predetermined unit; and an inferring unit configured to infer that one of an oil or an electrolyte contained in the coolant is abnormal when the ratio calculated by the ratio calculation unit exceeds an upper limit value of a control range and when the ratio calculated by the ratio calculation unit falls below a lower limit value of the control range, the control range being determined for the ratio in advance.

According to a second aspect of the present invention, there is provided a monitoring method for monitoring a coolant used in a machine tool, the monitoring method comprising: a first detection step of detecting a first physical quantity; a second detection step of detecting a second physical quantity different from the first physical quantity; a ratio calculation step of calculating a ratio between a first value representing the first physical quantity in a predetermined unit, and a second value representing the second physical quantity in the predetermined unit; and an inferring step of inferring that one of an oil or an electrolyte contained in the coolant is abnormal when the ratio calculated in the ratio calculation step exceeds an upper limit value of a control range and when the ratio calculated in the ratio calculation step falls below a lower limit value of the control range, the control range being determined for the ratio in advance.

According to the aspects of the present invention, a monitoring device and a monitoring method capable of grasping a change in the condition of a coolant in detail are provided.

BRIEF DESCRIPTION OF DRAWINGS

FIG. 2 is a flowchart showing the procedure of a monitoring process.

DETAILED DESCRIPTION OF THE INVENTION

Figure 1:
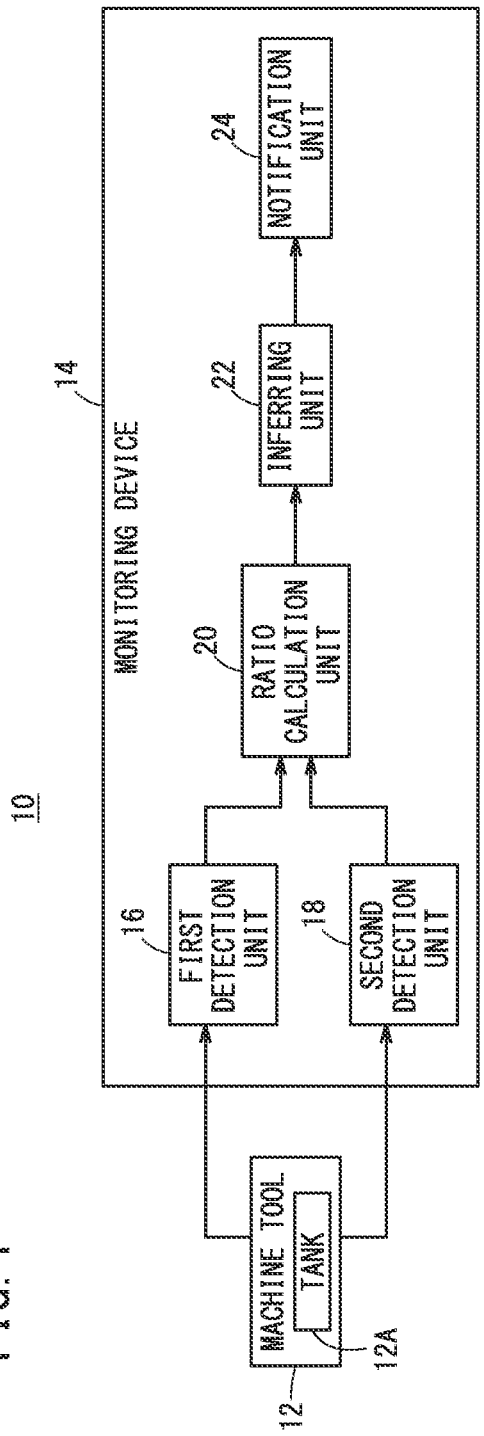
FIG. 1 is a schematic diagram showing a monitoring system according to an embodiment.

A preferred embodiment of the present invention will be described in detail below with reference to the accompanying drawings.

Embodiment

FIG. 1 is a schematic diagram showing a monitoring system 10 according to an embodiment. The monitoring system 10 includes a machine tool 12 and a monitoring device 14.

The machine tool 12 machines a workpiece by moving a tool relative to the workpiece. Examples of the type of machining include cutting and polishing. The machine tool 12 injects a coolant to a contact portion between the workpiece and the tool when the workpiece is being machined. The machine tool 12 includes a tank 12A for storing a coolant. When machining a workpiece, the machine tool 12 supplies the coolant stored in the tank 12A to a contact portion between the workpiece and the tool. The coolant contains an oil and an electrolyte.

The monitoring device 14 monitors the coolant used in the machine tool 12. The monitoring device 14 may be a control device that controls the machine tool 12, or may be a device different from the control device. The monitoring device 14 includes a first detection unit 16, a second detection unit 18, a ratio calculation unit 20, an inferring unit 22, and a notification unit 24.

The first detection unit 16 is a sensor that detects a first physical quantity. The first detection unit 16 is provided in the tank 12A or a coolant flow path in the machine tool 12. The first physical quantity is preferably correlated with the oil contained in the coolant. Examples of such a first physical quantity include, for example, a dielectric constant or a hydrogen ion concentration. When the first physical quantity is a dielectric constant, specific examples of the first detection unit 16 include a capacitance sensor. When the first physical quantity is a hydrogen ion concentration, specific examples of the first detection unit 16 include a hydrogen ion concentration meter. In the present embodiment, the first physical quantity is a hydrogen ion concentration.

The second detection unit 18 is a sensor that detects a second physical quantity different from the first physical quantity. The second detection unit 18 is provided in, for example, the tank 12A or the coolant flow path in the machine tool 12. The second physical quantity is preferably correlated with the electrolyte contained in the coolant. Examples of such a second physical quantity include, for example, an electrical conductivity. When the second physical quantity is an electrical conductivity, specific examples of the second detection unit 18 include a conductivity sensor. In the present embodiment, the second physical quantity is an electrical conductivity. When the second physical quantity is the electrical conductivity, the amount of the electrolyte contained in the coolant can be directly acquired, and the behavior of the electrolyte can be grasped more accurately than by other physical quantities.

The ratio calculation unit 20 calculates a ratio between a first value representing the first physical quantity (hydrogen ion concentration) in a predetermined unit, and a second value representing the second physical quantity (electrical conductivity) in a predetermined unit. The predetermined unit of the first value may be the same as or different from the predetermined unit of the second value. Specific examples of the ratio calculation unit 20 include a processor represented by a CPU or an MPU. The ratio calculation unit 20 acquires the first physical quantity (hydrogen ion concentration) from the first detection unit 16, and acquires the second physical quantity (electrical conductivity) from the second detection unit 18. In the present embodiment, the ratio calculation unit 20 calculates a ratio of the second value to the first value. That is, the ratio calculation unit 20 calculates a ratio in which the first value is the denominator and the second value is the numerator (second value/first value).

The inferring unit 22 infers that one of the oil or the electrolyte contained in the coolant is abnormal. Specific examples of the inferring unit 22 include a processor represented by a CPU or an MPU. The inferring unit 22 includes a memory that holds an upper limit value and a lower limit value of a control range. The inferring unit 22 may read an upper limit value and a lower limit value of a control range stored in a memory of the monitoring device 14, and hold the upper limit value and lower limit value that have been read.

In the present embodiment, the ratio calculated by the ratio calculation unit 20 is the ratio of the second value to the first value (second value/first value). The first value is a value correlated with the oil contained in the coolant and is a value obtained by converting the first physical quantity. The second value is a value correlated with the electrolyte contained in the coolant and is a value obtained by converting the second physical quantity. Therefore, the ratio of the second value to the first value indicates the ratio between the oil and the electrolyte in the coolant.

The ratio of the second value to the first value decreases as the amount of the oil becomes larger than the amount of the electrolyte in the coolant. Therefore, when the ratio of the second value to the first value falls below the lower limit value of the control range, it means that there is a high possibility that the amount of the oil in the coolant excessively increases. Examples of the case where the amount of the oil in the coolant excessively increases include a case where an oil different from the oil originally contained in the coolant is mixed into the coolant. When an oil different from the oil originally contained in the coolant is mixed into the coolant, the amount of the electrolyte in the coolant does not substantially change.

On the other hand, the ratio of the second value to the first value increases as the amount of the electrolyte becomes larger than the amount of the oil in the coolant. Therefore, when the ratio of the second value to the first value exceeds the upper limit value of the control range, it means that there is a high possibility that the amount of the electrolyte in the coolant excessively increases. Examples of the case where the amount of the electrolyte in the coolant excessively increases include a case where the coolant excessively evaporates.

Note that when both the amount of the oil and the amount of the electrolyte in the coolant increase or decrease, the ratio of the second value to the first value does not substantially change. Therefore, the ratio of the second value to the first value falls within the control range, and the coolant is normal. On the other hand, when one of the amount of the oil or the amount of the electrolyte in the coolant increases and the other decreases, and if the ratio of the second value to the first value is out of the control range, the coolant is abnormal.

When the ratio of the second value to the first value falls below the lower limit value of the control range, the inferring unit 22 infers that the oil contained in the coolant is abnormal. On the other hand, when the ratio of the second value to the first value exceeds the upper limit value, the inferring unit 22 infers that the electrolyte contained in the coolant is abnormal. When the ratio of the second value to the first value is within the control range, the inferring unit 22 infers that the coolant is normal.

The notification unit 24 provides a notification of a result inferred by the inferring unit 22. Specific examples of the notification unit 24 include a processor represented by a CPU or an MPU. The notification unit 24 provides a notification of the result inferred by the inferring unit 22 by controlling at least one of a speaker, a light emitting unit, or a display unit. At least one of the speaker, the light emitting unit, or the display unit may be provided in the monitoring device 14 or may be provided in a device external to the monitoring device 14.

When controlling the speaker, the notification unit 24 may provide a notification of the result inferred by the inferring unit 22, by generating a sound indicating the result inferred by the inferring unit 22. When controlling the light emitting unit, the notification unit 24 may provide a notification of the result inferred by the inferring unit 22, by causing the light emitting unit to blink in a blinking state corresponding to the result inferred by the inferring unit 22. When controlling the display unit, the notification unit 24 may provide a notification of the result inferred by the inferring unit 22, by causing the display unit to display a character indicating the result inferred by the inferring unit 22.

The notification unit 24 may present, together with the result inferred by the inferring unit 22, an improvement measure for improving the result. For example, when it is inferred that the oil contained in the coolant is abnormal, the notification unit 24 causes the display unit to display a warning message such as "There is a possibility that an oil different from the component of the coolant is mixed into the coolant. Please replace the coolant." On the other hand, when it is inferred that the electrolyte contained in the coolant is abnormal, the notification unit 24 causes the display unit to display a warning message such as "There is a possibility that the coolant excessively evaporates. Please refill with water."

Next, regarding a monitoring method of the monitoring device 14, the flow of a monitoring process of the monitoring device 14 will be described. FIG. 2 is a flowchart showing the procedure of the monitoring process.

In step S1, the first detection unit 16 detects a hydrogen ion concentration as the first physical quantity correlated with the oil contained in the coolant. When the first detection unit 16 detects the first physical quantity per unit time, the monitoring process proceeds to step S2.

In step S2, the second detection unit 18 detects an electrical conductivity as the second physical quantity correlated with the electrolyte contained in the coolant. When the second detection unit 18 detects the second physical quantity per unit time, the monitoring process proceeds to step S3.

In step S3, the ratio calculation unit 20 calculates the ratio (second value/first value) based on the first physical quantity (hydrogen ion concentration) detected in step S1 and the second physical quantity (electrical conductivity) detected in step S2. The first value is a value representing the first physical quantity (hydrogen ion concentration) in a predetermined unit, and the second value is a value representing the second physical quantity (electrical conductivity) in a predetermined unit. When the ratio calculation unit 20 calculates the ratio, the monitoring process proceeds to step S4.

In step S4, the inferring unit 22 compares the ratio calculated in step S3 with an upper limit value and a lower limit value of a ratio control range determined in advance. Here, when the ratio is equal to or less than the upper limit value of the control range and is equal to or greater than the lower limit value of the control range (when the ratio is within the control range), the inferring unit 22 infers that the coolant is normal. In this case, the monitoring process returns to step S1.

On the other hand, when the ratio calculated in step S3 is lower than the lower limit value of the control range, the inferring unit 22 infers that the oil contained in the coolant is abnormal. Further, when the ratio calculated in step S3 exceeds the upper limit value of the control range, the inferring unit 22 infers that the electrolyte contained in the coolant is abnormal. When the inferring unit 22 infers that one of the oil or the electrolyte contained in the coolant is abnormal, the monitoring process proceeds to step S5.

In step S5, the notification unit 24 provides a notification of the result inferred in step S4. For example, when a setting for requesting presentation of a coolant improvement measure is made by an input unit of the monitoring device 14, the notification unit 24 presents, together with the result inferred in step S4, an improvement measure for improving the result. When a predetermined time has elapsed since the notification unit 24 started providing the notification, the monitoring process ends.

In this manner, the monitoring device 14 of the present embodiment infers that one of the oil or the electrolyte contained in the coolant is abnormal based on the ratio between the first value and the second value. As a result, the monitoring device 14 can grasp the condition of the coolant in detail.

[Modification]

The ratio calculation unit 20 may calculate a ratio of the first value to the second value, instead of the ratio of the second value to the first value (second value/first value). Specifically, the ratio calculation unit 20 may calculate a ratio in which the second value is the denominator and the first value is the numerator (first value/second value).

In the present modification, the ratio of the first value to the second value increases as the amount of the oil becomes larger than the amount of the electrolyte in the coolant. Further, in the present modification, the ratio of the first value to the second value decreases as the amount of the electrolyte becomes larger than the amount of the oil in the coolant.

Therefore, in the present modification, when the ratio of the first value to the second value exceeds the upper limit value of the control range, the inferring unit 22 infers that the oil contained in the coolant is abnormal. Further, when the ratio of the first value to the second value falls below the lower limit value of the control range, the inferring unit 22 infers that the electrolyte is abnormal.

As a result, the monitoring device 14 can grasp the condition of the coolant in detail as in the above-described embodiment.

[Invention]

The first invention and the second invention will be described below as inventions that can be grasped from the above-described embodiment and modification.

(First Invention)

The first invention is the monitoring device (14) that monitors the coolant used in the machine tool (12). The monitoring device (14) includes: the first detection unit (16) configured to detect the first physical quantity; the second detection unit (18) configured to detect the second physical quantity different from the first physical quantity; the ratio calculation unit (20) configured to calculate the ratio between the first value representing the first physical quantity in the predetermined unit and the second value representing the second physical quantity in the unit; and the inferring unit (22) configured to infer that one of the oil or the electrolyte contained in the coolant is abnormal when the ratio calculated by the ratio calculation unit (20) exceeds the upper limit value of the control range and when the ratio calculated by the ratio calculation unit (20) falls below the lower limit value of the control range, the control range being determined for the ratio in advance. As a result, the condition of the coolant can be grasped in detail.

The inferring unit (22) may infer that the oil is abnormal when the ratio of the second value to the first value falls below the lower limit value of the control range or when the ratio of the first value to the second value exceeds the upper limit value of the control range. As a result, the condition of the coolant can be grasped in detail.

The inferring unit (22) may infer that the electrolyte is abnormal when the ratio of the second value to the first value exceeds the upper limit value of the control range or when the ratio of the first value to the second value falls below the lower limit value of the control range. As a result, the condition of the coolant can be grasped in detail.

The notification unit (24) configured to provide a notification of the result inferred by the inferring unit (22) may be provided. As a result, an operator can be alerted to the abnormality of the coolant component.

The notification unit (24) may present the improvement measure for improving the result inferred by the inferring unit (22). As a result, it becomes possible for the operator to easily identify the cause of the abnormality of the coolant component, and it becomes easy to return the coolant to the normal condition.

(Second Invention)

The second invention is the monitoring method for monitoring the coolant used in the machine tool (12). The monitoring method includes: the first detection step (S1) of detecting the first physical quantity; the second detection step (S2) of detecting the second physical quantity different from the first physical quantity; the ratio calculation step (S3) of calculating the ratio between the first value representing the first physical quantity in the predetermined unit and the second value representing the second physical quantity in the unit; and the inferring step (S4) of inferring that one of the oil or the electrolyte contained in the coolant is abnormal when the ratio calculated in the ratio calculation step (S3) exceeds the upper limit value of the control range and when the ratio calculated in the ratio calculation step (S3) falls below the lower limit value of the control range, the control range being determined for the ratio in advance. As a result, the condition of the coolant can be grasped in detail.

The inferring step (S4) may include inferring that the oil is abnormal when the ratio of the second value to the first value falls below the lower limit value of the control range or when the ratio of the first value to the second value exceeds the upper limit value of the control range. As a result, the condition of the coolant can be grasped in detail.

The inferring step (S4) may include inferring that the electrolyte is abnormal when the ratio of the second value to the first value exceeds the upper limit value of the control range or when the ratio of the first value to the second value falls below the lower limit value of the control range. As a result, the condition of the coolant can be grasped in detail.

The monitoring method may further include the notification step (S5) of providing a notification of the result inferred in the inferring step (S4). As a result, the operator can be alerted to the abnormality of the coolant component.

The notification step (S5) may include presenting the improvement measure for improving the result inferred in the inferring step (S4). As a result, it becomes possible for the operator to easily identify the cause of the abnormality of the coolant component, and it becomes easy to return the coolant to the normal condition.

The invention claimed is:

1. A monitoring device that monitors a coolant used in a machine tool, the monitoring device comprising:
   a first detection unit configured to detect a first physical quantity;
   a second detection unit configured to detect a second physical quantity different from the first physical quantity;
   a ratio calculation unit configured to calculate a ratio between a first value representing the first physical quantity in a predetermined unit, and a second value representing the second physical quantity in the predetermined unit; and
   an inferring unit configured to infer that one of an oil or an electrolyte contained in the coolant is abnormal when the ratio calculated by the ratio calculation unit exceeds an upper limit value of a control range and when the ratio calculated by the ratio calculation unit falls below a lower limit value of the control range, the control range being determined for the ratio in advance.

2. The monitoring device according to claim 1, wherein the inferring unit infers that the oil is abnormal when the ratio of the second value to the first value falls below the lower limit value of the control range or when the ratio of the first value to the second value exceeds the upper limit value of the control range.

3. The monitoring device according to claim 1, wherein the inferring unit infers that the electrolyte is abnormal when the ratio of the second value to the first value exceeds the upper limit value of the control range or when the ratio of the first value to the second value falls below the lower limit value of the control range.

4. The monitoring device according to claim 1, further comprising
   a notification unit configured to provide a notification of a result inferred by the inferring unit.

5. The monitoring device according to claim 4, wherein the notification unit presents an improvement measure for improving the result inferred by the inferring unit.

6. A monitoring method for monitoring a coolant used in a machine tool, the monitoring method comprising:
   a first detection step of detecting a first physical quantity;
   a second detection step of detecting a second physical quantity different from the first physical quantity;
   a ratio calculation step of calculating a ratio between a first value representing the first physical quantity in a predetermined unit, and a second value representing the second physical quantity in the predetermined unit; and
   an inferring step of inferring that one of an oil or an electrolyte contained in the coolant is abnormal when the ratio calculated in the ratio calculation step exceeds an upper limit value of a control range and when the ratio calculated in the ratio calculation step falls below a lower limit value of the control range, the control range being determined for the ratio in advance.

7. The monitoring method according to claim 6, wherein the inferring step includes inferring that the oil is abnormal when the ratio of the second value to the first value falls below the lower limit value of the control range or when the ratio of the first value to the second value exceeds the upper limit value of the control range.

8. The monitoring method according to claim 6, wherein the inferring step includes inferring that the electrolyte is abnormal when the ratio of the second value to the first value exceeds the upper limit value of the control range or when the ratio of the first value to the second value falls below the lower limit value of the control range.

9. The monitoring method according to claim 6, further comprising
   a notification step of providing a notification of a result inferred in the inferring step.

10. The monitoring method according to claim 9, wherein the notification step includes presenting an improvement measure for improving the result inferred in the inferring step.

* * * * *